United States Patent
Liang et al.

(10) Patent No.: US 10,072,020 B1
(45) Date of Patent: Sep. 11, 2018

(54) ISATIN SPIRO COMPOUNDS WITH ANTIBACTERIAL ACTIVITIES AND A METHOD OF PREPARING THE SAME

(71) Applicants: Chengyuan Liang, Xi'an (CN); Danni Tian, Xi'an (CN); Shunjun Ding, Xi'an (CN)

(72) Inventors: Chengyuan Liang, Xi'an (CN); Danni Tian, Xi'an (CN); Shunjun Ding, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 15/957,867

(22) Filed: Apr. 19, 2018

(30) Foreign Application Priority Data

Apr. 3, 2018 (CN) .......................... 2018 1 0285257

(51) Int. Cl.
C07D 491/107 (2006.01)
(52) U.S. Cl.
CPC ................ *C07D 491/107* (2013.01)

(58) Field of Classification Search
CPC .................................................. C07D 491/107
USPC .......................................................... 548/410
See application file for complete search history.

(56) References Cited

U.S. PATENT DOCUMENTS

9,487,535 B2 * 11/2016 Sun ...................... C07D 209/34

* cited by examiner

*Primary Examiner* — Kristin A Vajda (57) ABSTRACT

An isatin spiro compound having the following formula (I):

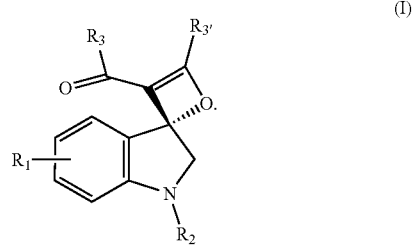

$R_1$ is halogen or $C_{1-3}$ alkyl; $R_2$ is $C_{1-3}$ alkyl or benzyl; and $R_3$ and $R_{3'}$ are independently H, $C_{1-3}$ alkyl or phenyl.

9 Claims, 2 Drawing Sheets

ISATIN SPIRO COMPOUNDS WITH ANTIBACTERIAL ACTIVITIES AND A METHOD OF PREPARING THE SAME

The present invention claims priority to Chinese Patent Application No. 201810285257.4, filed on Apr. 3, 2018, which is incorporated by reference for all purposes as if fully set forth herein.

FIELD OF THE INVENTION

The present invention relates to the field of medicinal chemistry, and in particular, to isatin spiro compounds with antibacterial activities and a method of preparing the same.

BACKGROUND OF THE INVENTION

Isatin is an active substance that widely exists in animals, plants and human bodies, and has some antibacterial effects in itself. Four isatin derivatives (Compounds A-D) showed antibacterial activities on Gram-positive bacteria. But these compounds had weaker antibacterial activities against Gram-negative bacteria.

A

B

C

D

There remains a need for new compounds that have antibacterial activities against Gram-negative bacteria.

SUMMARY OF THE INVENTION

In one embodiment, the present invention provides an isatin spiro compound having the following formula (I):

(I)

$R_1$ is halogen or $C_{1-3}$ alkyl; $R_2$ is $C_{1-3}$ alkyl or benzyl; and $R_3$ and $R_{3'}$ are independently H, $C_{1-3}$ alkyl or phenyl.

In another embodiment, in formula (I), $R_1$ is Cl or Br.

In another embodiment, in formula (I), $R_2$ is methyl, ethyl, propyl, or benzyl.

In another embodiment, in formula (I), $R_3$ and $R_{3'}$ are independently H or phenyl.

In another embodiment, the compound of formula (I) is selected form the group consisting of:

-continued

, and

In one embodiment, the present application provides a method of preparing the isatin spiro compound of formula (I). The method includes: reacting a compound of formula (II) with a compound of formula (III) and a compound of formula (IV) in a one pot reaction.

In formulas (I), (II), (III), and (IV), $R_1$ is halogen or $C_{1-3}$ alkyl; $R_2$ is $C_{1-3}$ alkyl or benzyl; and $R_3$ and $R_{3'}$ are independently H, $C_{1-3}$ alkyl or phenyl. The non-polar solvent is selected from the group consisting of benzene, $CCl_4$, toluene, and THF; and the catalyst includes a strong acid cation exchange resin, ferrocene, and palladium acetate.

In another embodiment, a molar ratio of the compound of formula (II) to the compound of formula (III) is 1:1 to 1:1.5.

In another embodiment, a molar ratio of the compound of formula (II) to the compound of formula (IV) is 1:1 to 1:1.2.

In another embodiment, the strong acid cation exchange resin includes a 7% crosslinked styrene divinylene copolymer with sulfonic acid group (—$SO_3H$).

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention.

As used herein, the term $C_{1-3}$ alkyl refers to a monovalent straight or branched chain, saturated aliphatic hydrocarbon radical having 1-3 carbon atoms. For example, $C_{1-3}$ alkyl refers to methyl, ethyl, propyl, and isopropyl. The term halogen refers to fluorine, chlorine, bromine and iodine.

It is an object of the present invention to provide isatin spiro compounds with antibacterial activities and a method of preparing the same. The method has the advantages of one-pot synthesis, low production cost, high operational safety, mild conditions, high yields, suitable for industrial production. The isatin spiro compounds can be used in antibacterial research and to treat various bacterial infections.

To achieve the above objects, the technical solution adopted by the present invention is described in details below.

An isatin spiro compound with antibacterial activities has the following formula (I):

$R_1$ is halogen or $C_{1-3}$ alkyl; $R_2$ is $C_{1-3}$ alkyl or benzyl; and $R_3$ and $R_{3'}$ are independently H, $C_{1-3}$ alkyl or benzyl.

An object of the present invention is to provide a method of preparing the isatin spiro compound of formula (I). The isatin spiro compound of formula (I) can be prepared by a one-pot synthesis reaction shown below.

$R_1$ is halogen or $C_{1-3}$ alkyl; $R_2$ is $C_{1-3}$ alkyl or benzyl; and $R_3$ and $R_{3'}$ are independently H, $C_{1-3}$ alkyl or benzyl.

The method includes the following steps:

(1) an isatin derivative (formula (II)), a fatty alcohol (formula (III)), and a dicarbonyl compound (formula (IV)), in a molar ratio of 1:1-1.5:1-1.2, were added to a reactor. A non-polar solvent, in less than ⅔ of reactor's volume, was added to the reactor, and the mixture was mixed thoroughly. The non-polar solvent can be benzene, $CCl_4$, toluene, or tetrahydrofuran (THF). At the presence of strong acid cation exchange resin, ferrocene, and palladium acetate as catalysts, the mixture was stirred and heated at 60-100° C. for 3-7 hours.

(2) The reaction was monitored with thin layer chromatograph (TLC). When TLC indicated that the reaction was complete, the reaction mixture was removed from heating.

(3) The reaction mixture was concentrated, filtrated, and purified by fresh chromatograph to obtain desired product.

Example 1

The Preparation of (R)-5-bromo-1-methyl-2-oxospiro[indoline-3,2'-oxete]-3'-carbaldehyde (Compound 1)

In a 100 mL round flask, 100 mg (0.44 mmol) 5-bromoisatin, 21 mg (0.66 mmol) methanol, 41 mg (0.53 mmol) malondialdehyde, catalytic amount (0.044 mmol) of cation exchange resin 007×7 (7% crosslinked styrene divinylene copolymer with sulfonic acid group (—$SO_3H$)), catalytic amount (0.044 mmol) of ferrocene, catalytic amount (0.044 mmol) of palladium acetate, and 50 mL $CCl_4$ as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 92.8 mg desired product (compound 1), a yield of 72%.

$^1$H-NMR (300 MHz, DMSO-$d_6$) δ (ppm): 12.32 (1 H, s), 8.33 (1 H, s), 8.21 (1 H, d, J=7.5 Hz), 8.17 (1 H, d, J=7.5 Hz), 8.01 (1 H, s), 3.78 (3 H, s); $^{13}$C-NMR (75 MHz, DMSO-$d_6$) δ (ppm): 167.2, 154.2, 143.7, 122.8, 118.8, 109.2, 106.1, 30.5; MS (ESI) for (M+H)$^+$: 293.9.

Example 2

The Preparation of (R)-7-bromo-1-methyl-2-oxospiro[indoline-3,2'-oxete]-3'-carbaldehyde (Compound 2)

In a 100 mL round flask, 80 mg (0.36 mmol) 7-bromoisatin, 17 mg (0.54 mmol) methanol, 31 mg (0.43 mmol) malondialdehyde, catalytic amount (0.036 mmol) of cation exchange resin 007×7 (7% crosslinked styrene divinylene copolymer with sulfonic acid group (—$SO_3H$)), catalytic amount (0.036 mmol) of ferrocene, catalytic amount (0.036 mmol) of palladium acetate, and 50 mL $CCl_4$ as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 72.9 mg of desired product (compound 2), a yield of 70%.

-continued

¹H-NMR (300 MHz, DMSO-d$_6$) δ (ppm): 12.21 (1 H, s), 8.43 (1 H, d), 8.21 (1 H, m, J=7.5 Hz, J=10.5 Hz), 8.13 (1 H, d, J=10.5 Hz), 8.03 (1 H, s), 3.44 (3 H, s); ¹³C-NMR (75 MHz, DMSO-d$_6$) δ (ppm): 171.2, 144.3, 139.0, 125.4, 110.2, 101.4, 98.3, 32.1; MS (ESI) for (M+Na)$^+$: 315.9.

Example 3

The Preparation of (R)-5-chloro-1-methyl-2-oxospiro[indoline-3,2'-oxete]-3'-carbaldehyde (Compound 3)

In a 100 mL round flask, 100 mg (0.56 mmol) 5-chloroisatin, 27 mg (0.84 mmol) methanol, 48 mg (0.67 mmol) malondialdehyde, catalytic amount (0.056 mmol) of cation exchange resin 007×7 (7% crosslinked styrene divinylene copolymer with sulfonic acid group (—SO$_3$H)), catalytic amount (0.056 mmol) of ferrocene, catalytic amount (0.056 mmol) of palladium acetate, and 50 mL THF as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 107.4 mg of desired product (compound 3), a yield of 77%.

¹H-NMR (300 MHz, DMSO-d$_6$) δ (ppm): 11.7 (1 H, s), 8.51 (1 H, s), 8.32 (1 H, d, J=7.5 Hz), 8.21(1 H, d, J=7.5 Hz), 8.10 (1 H, s), 3.04 (3 H, s); ¹³C-NMR (75 MHz, DMSO-d$_6$) δ (ppm): 172.9, 146.7, 139.0, 123.0, 110.4, 109.2, 107.9, 103.5, 95.9, 31.4; MS (ESI) for (M+H)$^+$: 250.1.

Example 4

The Preparation of (R)-7-chloro-1-methyl-2-oxospiro[indoline-3,2'-oxete]-3'-carbaldehyde (Compound 4)

In a 100 mL round flask, 80 mg (0.44 mmol) 7-chloroisatin, 21.1 mg (0.66 mmol) methanol, 38.2 mg (0.53 mmol) malondialdehyde, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 50 mL CCl$_4$ as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 81.1 mg of desired product (compound 4), a yield of 74%.

¹H-NMR (300 MHz, DMSO-d$_6$) δ (ppm): 12.44 (1 H, s), 8.61 (1 H, d), 8.47 (1 H, dd, J=7.5 Hz, J=10.0 Hz), 8.38 (1 H, d, J=7.5 Hz), 8.21 (1 H, s), 3.69 (3 H, s); ¹³C-NMR (75 MHz, DMSO-d$_6$) δ (ppm): 178.2, 151.3, 146.2, 132.8, 117.1, 108.5, 105.1, 96.4, 29.9; MS (ESI) for (M+Na)$^+$: 272.0.

Example 5

The Preparation of (R)-3'-benzoyl-5-bromo-1-methyl-4'-phenylspiro[indoline-3,2'-oxet]-2-one (Compound 5)

In a 100 mL round flask, 100 mg (0.45 mmol) 5-bromoisatin, 21.8 mg (0.68 mmol) methanol, 121 mg (0.54 mmol) 1,3-diphenylpropane dione, catalytic amount (0.045 mmol) of cation exchange resin 007×7 (7% crosslinked styrene divinylene copolymer with sulfonic acid group (—SO$_3$H)), catalytic amount (0.045 mmol) of ferrocene, catalytic amount (0.045 mmol) of palladium acetate, and 50 mL benzene as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 142.2 mg of desired product (compound 5), a yield of 71%.

¹H-NMR (300 MHz, DMSO-d$_6$) δ (ppm): 8.40-8.67 (4 H, m, J32 7.5 Hz, J=10.5 Hz), 8.02-8.21 (6 H, m, J=10.5 Hz, J=7.5 Hz), 7.92-7.99 (2 H, m), 7.88 (1 H, d), 3.62 (3 H, s);

$^{13}$C-NMR (75 MHz, DMSO-d$_6$) δ (ppm): 165.5, 141.7, 139.0, 118.9, 114.5, 109.8, 105.0, 104.2, 103.5, 94.2, 73.2, 67.5, 25.5; MS (ESI) for (M+H)$^+$: 469.1.

Example 6

The Preparation of (R)-3'-benzoyl-7-bromo-1-methyl-4'-phenylspiro[indoline-3,2'-oxet]-2-one (Compound 6)

In a 100 mL round flask, 80 mg (0.36 mmol) 7-bromoisatin, 17.3 mg (0.54 mmol) methanol, 96.3 mg (0.43 mmol) 1,3-diphenylpropane dione, catalytic amount (0.036 mmol) of cation exchange resin 007×7 (7% crosslinked styrene divinylene copolymer with sulfonic acid group (—SO$_3$H)), catalytic amount (0.036 mmol) of ferrocene, catalytic amount (0.036 mmol) of palladium acetate, and 25 mL benzene as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 112.1 mg of desired product (compound 6), a yield of 70%.

$^1$H-NMR (300 MHz, DMSO-d$_6$) δ (ppm): 8.24-8.33 (4 H, m), 8.22 (1 H, d), 6.96-8.07 (6 H, m), 7.75-7.77 (2 H, dd, J=7.25 Hz, J=7.25 Hz), 3.92 (3 H, s); $^{13}$C-NMR (75 MHz, DMSO-d$_6$) δ (ppm): 180.3, 162.7, 160.0, 139.5, 137.8, 132.3, 127.0, 123.4, 121.2, 116.3, 109.2, 94.8, 85.2, 30.5; MS (ESI) for (M+Na)$^+$: 468.0.

Example 7

The Preparation of (R)-3'-benzoyl-5-chloro-1-methyl-4'-phenylspiro[indoline-3,2'-oxet]-2-one (Compound 7)

In a 100 mL round flask, 100 mg (0.55 mmol) 5-chloroisatin, 26.4 mg (0.83 mmol) methanol, 147.8 mg (0.66 mmol) 1,3-diphenylpropane dione, catalytic amount (0.055 mmol) of cation exchange resin 007×7 (7% crosslinked styrene divinylene copolymer with sulfonic acid group (—SO$_3$H)), catalytic amount (0.055 mmol) of ferrocene, catalytic amount (0.055 mmol) of palladium acetate, and 30 mL CCl$_4$ as solvent were added to the flask. The reaction mixture was heated at 90° C. for 6 hours. The reaction was monitored with TLC. When TLC indicated that reaction was complete, heating was removed. The reaction mixture was concentrated, filtered, and purified by fresh chromatograph to obtain 178.7 mg of desired product (compound 7), a yield of 73%.

$^1$H-NMR (300 MHz, DMSO-d$_6$) δ (ppm): 8.41-8.63 (4 H, m), 8.24 (1 H, s), 7.85-7.93 (6 H, m), 7.71 (1 H, m), 7.64 (1 H, d), 3.55 (3 H, s); $^{13}$C-NMR (75 MHz, DMSO-d$_6$) δ (ppm): 170.5, 145.6, 144.0, 121.3, 117.9, 114.3, 110.4, 107.8, 104.4, 102.7, 100.3, 82.5, 33.4; MS (ESI) for (M+H)$^+$: 402.1.

Example 8

The Preparation of (R)-3'-benzoyl-7-chloro-1-methyl-4'-phenylspiro[indoline-3,2'-oxet]-2-one (Compound 8)

In a 100 mL round flask, 80 mg (0.44 mmol) 7-chloroisatin, 21.1 mg (0.66 mmol) methanol, 118.7 mg (0.53 mmol) 1,3-diphenylpropane dione, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 25 mL THF as solvent were added to the flask. The reaction mixture was heated at 90° C. for 6 hours. The reaction was monitored with TLC. When TLC indicated that reaction was complete, heating was removed. The reaction mixture was concentrated, filtered, and purified by fresh chromatograph to obtain 83.3 mg of desired product (compound 8), a yield of 76%.

$^1$H-NMR (300 MHz, DMSO-d$_6$) δ (ppm): 8.31-8.59 (4 H, m), 8.27 (1 H, d), 7.92-8.13 (6 H, m), 7.74 (1 H, t), 7.53 (1 H, d), 3.41 (3 H, s); $^{13}$C-NMR (75 MHz, DMSO-d$_6$) δ (ppm): 173.2, 152.6, 150.2, 133.1, 129.4, 125.3, 121.0, 113.9, 111.3, 107.5, 88.6, 31.2; MS (ESI) for (M+Na)$^+$: 424.1.

Example 9

The Preparation of (R)-3'-benzoyl-5-bromo-1-ethylspiro[indoline-3,2'-oxet]-2-one (Compound 9)

In a 100 mL round flask, 100 mg (0.44 mmol) 5-bromoisatin, 30.4 mg (0.66 mmol) ethanol, 118.7 mg (0.53 mmol) 1-phenylmalonaldehyde, catalytic amount (0.044 mmol) of cation exchange resin 007×7 (7% crosslinked styrene divinylene copolymer with sulfonic acid group (—SO₃H)), catalytic amount (0.044 mmol) of ferrocene, catalytic amount (0.044 mmol) of palladium acetate, and 30 mL benzene as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 121.3 mg of desired product (compound 9), a yield of 72%.

$^1$H-NMR (300 MHz, DMSO-$d_6$) δ (ppm): 8.84-9.09 (5 H, m), 8.78 (1 H, d), 8.76 (1 H, s), 8.62 (1 H, s), 8.29 (1 H, d), 4.62 (2 H, m), 3.51 (3 H, t); $^{13}$C-NMR (75 MHz, DMSO-$d_6$) δ (ppm): 187.5, 153.4, 138.5, 130.9, 126.5, 121.8, 117.0, 116.2, 115.5, 106.2, 104.3, 95.4, 44.5, 13.7; MS (ESI) for (M+H)⁺: 384.0.

Example 10

The Preparation of (R)-7-bromo-2-oxo-4'-phenyl-1-propylspiro[indoline-3,2'-oxete]-3'-carbaldehyde (Compound 10)

In a 100 mL round flask, 80 mg (0.36 mmol) 7-bromoisatin, 32.4 mg (0.54 mmol) propanol, 63.7 mg (0.43 mmol) 1-phenylmalonaldehyde, catalytic amount (0.036 mmol) of cation exchange resin 007×7 (7% crosslinked styrene divinylene copolymer with sulfonic acid group (—SO₃H)), catalytic amount (0.036 mmol) of ferrocene, catalytic amount (0.036 mmol) of palladium acetate, and 25 mL CCl₄ as solvent were added to the flask. The reaction mixture was heated at 100° C. for 6 hours. The reaction was monitored with TLC. When TLC indicated that reaction was complete, heating was removed. The reaction mixture was concentrated, filtered, and purified by fresh chromatograph to obtain 118.6 mg of desired product (compound 10), a yield of 83%.

$^1$H-NMR (300 MHz, DMSO-$d_6$) δ (ppm): 9.79 (1 H, s), 8.43-8.87 (5 H, m), 8.45 (1 H, d), 8.35 (1 H, t), 8.21 (1 H, d), 4.48 (2 H, t), 3.71 (2 H, m), 2.94 (3 H, t); $^{13}$C-NMR (75 MHz, DMSO-$d_6$) δ (ppm): 180.9, 159.5, 152.4, 133.4, 122.4, 118.7, 116.8, 116.6, 115.9, 113.6, 111.1, 92.9, 44.9, 22.6, 12.0; MS (ESI) for (M+Na)⁺: 420.1.

Example 11

The Preparation of (R)-3'-benzoyl-5-chloro-1-propylspiro[indoline-3,2'-oxet]-2-one (Compound 11)

In a 100 mL round flask, 100 mg (0.55 mmol) 5-chloroisatin, 49.8 mg (0.83 mmol) propanol, 97.7 mg (0.66 mmol) 1-phenylmalonaldehyde, catalytic amount (0.055 mmol) of cation exchange resin 007×7 (7% crosslinked styrene divinylene copolymer with sulfonic acid group (—SO₃H)), catalytic amount (0.055 mmol) of ferrocene, catalytic amount (0.055 mmol) of palladium acetate, and 30 mL toluene as solvent were added to the flask. The reaction mixture was heated at 110° C. for 6 hours. The reaction was monitored with TLC. When TLC indicated that reaction was complete, heating was removed. The reaction mixture was concentrated, filtered, and purified by fresh chromatograph to obtain 167 mg of desired product (compound 11), a yield of 86%.

$^1$H-NMR (300 MHz, DMSO-$d_6$) δ (ppm): 8.64-8.89 (5 H, m), 8.61 (1 H, s), 8.47 (1 H, d), 8.42 (1 H, s), 8.14 (1 H, d), 4.38 (2 H, t), 2.96 (2 H, m), 1.98 (3 H, t); $^{13}$C-NMR (75 MHz, DMSO-$d_6$) δ (ppm): 179.5, 155.4, 140.5, 132.0, 123.5, 119.4, 118.6, 118.2, 117.5, 116.9, 112.5, 82.6, 44.3, 22.8, 12.2; MS (ESI) for (M+H)⁺: 354.1.

Example 12

The Preparation of (R)-7-chloro-1-ethyl-2-oxo-4'-phenylspiro[indoline-3,2'-oxete]-3'-carbaldehyde (Compound 12)

In a 100 mL round flask, 80 mg (0.44 mmol) 7-chloroisatin, 30.4 mg (0.66 mmol) ethanol, 78.4 mg (0.53 mmol) 1-phenylmalonaldehyde, catalytic amount (0.044 mmol) of cation exchange resin 007×7 (7% crosslinked styrene divinylene copolymer with sulfonic acid group (—SO₃H)), catalytic amount (0.044 mmol) of ferrocene, catalytic amount (0.044 mmol) of palladium acetate, and 25 mL THF as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 120.8 mg of desired product (compound 12), a yield of 81%.

$^1$H-NMR (300 MHz, DMSO-d$_6$) δ (ppm): 10.08 (1 H, s), 8.87 (2 H, d), 8.65 (1 H, d), 7.84-7.93 (3 H, m), 7.71 (1 H, t), 7.42 (1 H, d), 3.33 (2 H, m), 2.03 (3 H, t); $^{13}$C-NMR (75 MHz, DMSO-d$_6$) δ (ppm): 182,3, 169.4, 162.8, 140.2, 128.4, 121.0, 119.4, 117.9, 114.3, 102.3, 76.4, 48.5, 17.8; MS (ESI) for (M+Na)$^+$: 362.1.

Example 13

The Preparation of (R)-5-bromo-1-ethyl-2-oxospiro[indoline-3,2'-oxete]-3'-carbaldehyde (Compound 13)

In a 100 mL round flask, 100 mg (0.44 mmol) 5-bromoisatin, 30.4 mg (0.66 mmol) ethanol, 38.2 mg (0.53 mmol) malondialdehyde, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 30 mL benzene as solvent were added to the flask. The reaction mixture was heated at 90° C. for 6 hours. The reaction was monitored with TLC. When TLC indicated that reaction was complete, heating was removed. The reaction mixture was concentrated, filtered, and purified by fresh chromatograph to obtain 114.8 mg of desired product (compound 13), a yield of 85%.

Figure 1:
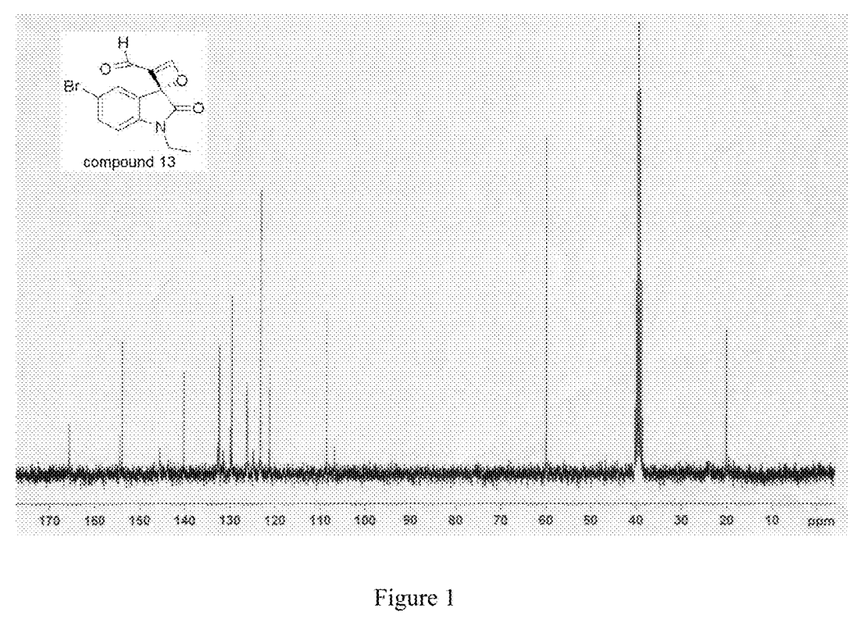
FIG. 1 is $^1$H-NMR spectrum of compound 13.
Figure 2:
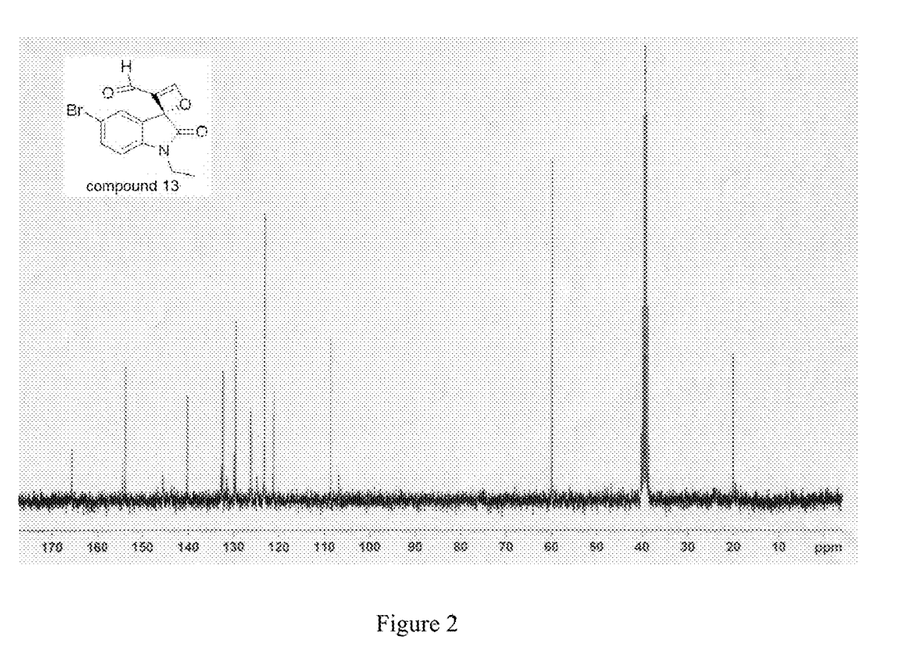
FIG. 2 is $^{13}$C-NMR spectrum of compound 13.

$^1$H-NMR (300 MHz, DMSO-d$_6$) δ (ppm): 8.77 (1 H, s), 8.40 (1 H, d), 8.37 (1 H, d), 8.03 (1 H, d), 3.48 (1 H, d), 3.45 (2 H, m), 2.60 (3 H, t) (shown in FIG. 1); $^{13}$C-NMR (75 MHz, DMSO-d$_6$) δ (ppm): 165.7, 153.9, 140.3, 132.4, 131.6, 129.6, 123.2, 121.2, 108.5, 59.9, 20.1 (shown in FIG. 2); MS (ESI) for (M+H)$^+$: 308.0.

Example 14

The Preparation of (R)-7-chloro-1-ethyl-2-oxospiro[indoline-3,2'-oxete]-3'-carbaldehyde (Compound 14)

In a 100 mL round flask, 80 mg (0.44 mmol) 7-chloroisatin, 71.3 mg (0.66 mmol) benzyl alcohol, 38.2 mg (0.53 mmol) malondialdehyde, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 50 mL benzene as solvent were added to the flask. The reaction mixture was heated at 90° C. for 6 hours. The reaction was monitored with TLC. When TLC indicated that reaction was complete, heating was removed. The reaction mixture was concentrated, filtered, and purified by fresh chromatograph to obtain 115.8 mg of desired product (compound 14), a yield of 81%.

$^1$H-NMR (300 MHz, DMSO-d$_6$) δ (ppm): 9.18 (1 H, s), 8.27 (1 H, d), 7.93-8.02 (2 H, m), 7.53-7.58 (5 H, m), 7.12 (1 H, s), 4.91 (2 H, s); $^{13}$C-NMR (75 MHz, DMSO-d$_6$) δ (ppm): 181.3, 155.7, 148.0, 140.1, 134.1, 128.1, 123.4, 119.2, 114.1, 113.7, 113.1, 112.7, 109.5, 87.2, 50.4; MS (ESI) for (M+Na)$^+$: 348.1.

Example 15

The preparation of (R)-3'-benzoyl-7-bromo-4'-phenyl-1-propylspiro[indoline-3,2'-oxet]-2-one (compound 15)

In a 100 mL round flask, 100 mg (0.44 mmol) 7-bromoisatin, 71.3 mg (0.66 mmol) benzyl alcohol, 118.8 mg (0.53 mmol) 1,3-diphenylpropane dione, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 30 mL CCl$_4$ as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 183.4 mg of desired product (compound 15), a yield of 80%.

$^1$H-NMR (300 MHz, DMSO-d$_6$) δ (ppm): 8.34 (1 H, d), 8.08-8.17 (4 H, m), 7.84-8.08 (6 H, m), 7.51 (1 H, t), 7.37 (1 H, d), 7.24-7.29 (5 H, m), 4.05 (2 H, t); $^{13}$C-NMR (75 MHz, DMSO-d$_6$) δ (ppm): 185.0, 162.1, 158.3, 134.5, 129.5, 123.2, 122.9, 122.1, 115.4, 107.3, 102.8, 100.2, 97.9, 88.6, 46.4; MS (ESI) for (M+H)$^+$: 522.1.

Example 16

The Preparation of (R)-3'-benzoyl-5-chloro-4'-phenyl-1-propylspiro[indoline-3,2'-oxet]-2-one (Compound 16)

In a 100 mL round flask, 80 mg (0.44 mmol) 5-chloroisatin, 39.6 mg (0.66 mmol) propanol, 118.8 mg (0.53 mmol) 1,3-diphenylpropane dione, catalytic amount (0.044 mmol) of cation exchange resin 007×7 (7% crosslinked styrene divinylene copolymer with sulfonic acid group (—SO$_3$H)), catalytic amount (0.044 mmol) of ferrocene, catalytic amount (0.044 mmol) of palladium acetate, and 50 mL THF as solvent were added to the flask. The reaction mixture was heated at 80° C. for 6 hours. The reaction was monitored with TLC. When TLC indicated that reaction was complete, heating was removed. The reaction mixture was concentrated, filtered, and purified by fresh chromatograph to obtain 156.7 mg of desired product (compound 16), a yield of 83%.

$^1$H-NMR (300 MHz, DMSO-d$_6$) δ (ppm): 8.21 (1 H, d), 8.02-8.14 (4 H, m), 7.86-7.93 (6 H, m), 7.61-7.63 (2 H, m), 3.64 (2 H, t), 2.05 (2 H, m), 1.97 (3 H, t); $^{13}$C-NMR (75 MHz, DMSO-d$_6$) δ (ppm): 181.9, 168.4, 156.4, 143.4, 129.4, 125.4, 123.6, 120.7, 119.1, 118.6, 117.5, 106.5, 102.3, 86.7, 42.4, 25.0, 14.1; MS (ESI) for (M+H)$^+$: 496.1.

Example 17

Antibacterial Activity Test of the Compounds of the Invention

The compounds were tested for their antibacterial activities using the following standard strains: *Escherichia coli* ATCC 25922, *Escherichia coli* 10-1, and *Escherichia coli* 10-2.

Preparation of *Escherichia coli* strains and bacterial liquid: the test strains (*Escherichia coli* ATCC 25922, *Escherichia coli* 10-1, and *Escherichia coli* 10-2) stock solutions were seeded in LB solid Media Petri dishes and placed in a 37° C. incubator overnight. The next day, single colonies were picked from LB solid petri dishes and inoculated into 6-10 mL LB liquid medium and cultured with shaking at 150 rpm for 3 hours at 37° C. 100 μL of the liquid was evenly coated on an LB solid plate, and inverted in an incubator at 37° C. overnight. Viable cells in the logarithmic growth phase were collected after 16-18 hours, and sterile water was added to form a bacteria suspension with the number of bacteria being 106 CFu·mL$^{-1}$.

Preparation of compound-containing agar plate: MH agar was heated to dissolve and placed in 45-50° C. water bath to balance, the compounds were added at different concentrations (160, 300, 600 μg·mL$^{-1}$). The mixtures were mixed evenly and poured onto sterilization plates, placed into a sealed plastic bag at 2-8° C.

Determination of the minimum inhibitory concentration: the minimum inhibitory concentrations (MICs) of the test compounds on the test bacteria were determined by diluting the agar plate two-fold. Multi-point inoculation instrument was used to inoculate bacteria to the MH agar medium that contains the compounds, forming a plaque with a diameter of 5 to 8 mm. After the plates were incubated at 25° C. for 18-24 hours, the growth state of the bacteria was observed, and the minimum compound concentration for inhibiting the growth of the bacteria was the MIC.

The results are shown in Table 1. The samples refer to the isatin spiro compounds, and the sample numbers correspond to compound numbers.

TABLE 1

Compounds' Minimum Inhibitory Concentrations (μg·mL$^{-1}$)

| | Strains | | |
| --- | --- | --- | --- |
| Samples | *Escherichia coli* ATCC 25922 | *Escherichia coli* 10-1 | *Escherichia coli* 10-2 |
| isatin | >600 | 300 | 160 |
| 1 | 300 | 160 | 160 |
| 2 | 300 | 160 | >160 |
| 3 | 300 | 160 | 300 |
| 4 | >600 | 300 | 160 |
| 5 | 160 | 300 | 300 |
| 6 | 300 | >600 | 300 |
| 7 | 300 | 160 | 300 |
| 8 | 160 | 300 | 300 |
| 9 | 300 | 300 | 160 |
| 10 | 300 | 160 | >600 |
| 11 | >600 | 160 | 160 |
| 12 | 300 | 160 | 300 |
| 13 | 160 | 300 | 160 |
| 14 | 300 | 160 | 160 |
| 15 | 160 | 160 | 300 |
| 16 | 160 | 300 | 160 |

As shown in Table 1, compounds 1-16 showed different degrees of antibacterial activities among the three tested *E. coli* strains. Among them, compounds 13-16 showed better activities better than isatin. In summary, the isatin spiro compounds of the present invention can be used as gram-negative bacteria antibacterial drug candidates and for further preclinical studies.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An isatin spiro compound having the following formula (I):

wherein $R_1$ is halogen or $C_{1-3}$ alkyl; $R_2$ is $C_{1-3}$ alkyl or benzyl; and $R_3$ and $R_{3'}$ are independently H, $C_{1-3}$ alkyl or phenyl.

2. The isatin spiro compound of claim 1, wherein $R_1$ is Cl or Br.

3. The isatin spiro compound of claim 1, wherein $R_2$ is methyl, ethyl, propyl, or benzyl.

4. The isatin spiro compound of claim 1, wherein $R_3$ and $R_{3'}$ are independently H or phenyl.

5. The isatin spiro compound of claim 1, wherein the compound is selected form the group consisting of:

6. A method of preparing the isatin spiro compound of claim 1 comprising:

reacting a compound of formula (II) with a compound of formula (III) and a compound of formula (IV) in a one pot reaction, wherein $R_1$ is halogen or $C_{1-3}$ alkyl; $R_2$ is $C_{1-3}$ alkyl or benzyl; and $R_3$ and $R_{3'}$ are independently H, $C_{1-3}$ alkyl or phenyl;

wherein the non-polar solvent is selected from the group consisting of benzene, $CCl_4$, toluene, and THF; and wherein the catalyst includes a strong acid cation exchange resin, ferrocene, and palladium acetate.

7. The method of the claim 6, wherein a molar ratio of the compound of formula (II) to the compound of formula (III) is 1:1 to 1:1.5.

8. The method of the claim 6, wherein a molar ratio of the compound of formula (II) to the compound of formula (IV) is 1:1 to 1:1.2.

9. The method of claim 6, wherein the strong acid cation exchange resin includes a 7% crosslinked styrene divinylene copolymer with sulfonic acid group (—$SO_3H$).

* * * * *